United States Patent [19]

Walker

[11] Patent Number: 4,512,796
[45] Date of Patent: Apr. 23, 1985

[54] HALOACETYLAMINOMETHYL DIOXOLANE HERBICIDE ANTIDOTES

[75] Inventor: Francis H. Walker, Mill Valley, Calif.

[73] Assignee: Stauffer Chemical Company, Westport, Conn.

[21] Appl. No.: 497,943

[22] Filed: May 25, 1983

Related U.S. Application Data

[62] Division of Ser. No. 286,328, Jul. 24, 1981, Pat. No. 4,406,686.

[51] Int. Cl.³ ............................................. A01N 43/28
[52] U.S. Cl. ........................................... 71/88; 71/100; 71/118
[58] Field of Search ............................... 71/88, 118

[56] References Cited

U.S. PATENT DOCUMENTS

| | | | |
|---|---|---|---|
| 4,113,464 | 9/1978 | Stach et al. | 549/452 |
| 4,154,595 | 5/1979 | Walker | 549/452 |
| 4,155,745 | 5/1979 | Walker | 549/452 |
| 4,294,764 | 10/1981 | Rinehart | 549/452 |
| 4,336,058 | 6/1982 | Felix | 71/88 |

Primary Examiner—Catherine L. Mills
Attorney, Agent, or Firm—Leona L. Lauder

[57] ABSTRACT

Herbicide antidote compounds having the formula:

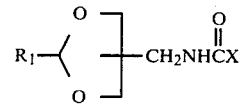

in which
X is halomethyl, wherein halo is selected from the group consisting of chlorine, bromine, and iodine and the methyl group is mono-, di-, or tri-substituted; and
$R_1$ is selected from the group consisting of lower alkyl having 1–4 carbon atoms, inclusive, and alkenyloxy having from 2–6 carbon atoms, inclusive, provided that, if $R_1$ is alkyl the haloacetylaminomethyl moiety is attached to the ring at the 2-position.

10 Claims, No Drawings

HALOACETYLAMINOMETHYL DIOXOLANE HERBICIDE ANTIDOTES

This is a division of application Ser. No. 286,328, filed July 24, 1981 now U.S. Pat. No. 4,406,686.

FIELD OF THE INVENTION

This invention relates to herbicide antidotes, and, more particularly, to haloacetylaminomethyl dioxolane compounds which are useful as herbicide antidotes.

BACKGROUND OF THE INVENTION

An herbicide is a compound which adversely controls or modifies plant growth, e.g., killing, retarding, defoliating, desiccating, regulating, stunting, tillering, stimulating, and dwarfing. The term "plant" refers to all physical parts of a plant, including seeds, seedlings, saplings, roots, tubers, stems, stalks, foliage, and fruits. "Plant growth" includes all phases of development from seed germination to natural or induced cessation of life.

Herbicides are generally used to control or eradicate weed pests. They have gained a high degree of commercial success because it has been shown that such control can increase crop yield and reduce harvesting costs.

The most popular methods of herbicide application include: pre-plant incorporation into the soil; in-furrow application to seeds and surrounding soil; pre-emergence surface treatment of seeded soil; and post-emergence treatment of the plant and soil.

A manufacturer of an herbicide generally recommends a range of application rates and concentrations calculated to maximize weed control. The range of rates varies from approximately 0.01 to 50 pounds per acre (0.0112 to 56 kilograms per hectare (k/ha)), and is usually in the range of from 0.1 to 25 pounds per acre (0.112 to 28 k/ha). The term "herbicidally effective amount" describes the amount of an herbicide compound which controls or modifies plant growth. The actual amount used depends upon several considerations, including particular weed susceptibility and overall cost limitations.

The most important factor influencing the usefulness of a given herbicide is its selectivity towards crops. In some cases, a beneficial crop is susceptible to the effects of the herbicide. In addition, certain herbicidal compounds are phytotoxic to some weed species but not to others. To be effective, an herbicide must cause minimal damage (preferably no damage) to the beneficial crop while maximizing damage to weed species which plague that crop.

To preserve the beneficial aspects of herbicide use and to minimize crop damage, many herbicide antidotes have been prepared. These antidotes reduce or eliminate damage to the crop without substantially impairing the damaging effect of the herbicide on weed species; See U.S. Pat. Nos. 4,021,224 and 4,021,229 and Belgian Pat. No. 846,894.

The precise mechanism by which an antidote reduces herbicidal crop injury has not been established. An antidote compound may be a remedy, interferent, protectant, or antagonist. As used herein, "antidote" describes a compound which has the effect of establishing herbicide selectivity, i.e., continued herbicidal phytotoxicity to weed species and reduced or non-phytotoxicity to cultivated crop species. The term "antidotally effective amount" describes the amount of an antidote compound which counteracts a phytotoxic response of a beneficial crop to an herbicide.

Thiocarbamate herbicides and acetanilide herbicides are particularly effective in the control of grassy type weeds which interfere with the cultivation of a wide variety of crops, e.g., barley, corn, cotton, lentils, peanuts, peas, potatoes, soybeans, spinach, tobacco and tomatoes. Frequently the effective use of these herbicides requires the addition of an antidote compound.

DESCRIPTION OF THE INVENTION

It has now been discovered that certain haloacetylaminomethyl compounds are effective antidotes for the protection of a variety of crops from thiocarbamate herbicide and acetanilide herbicide injuries. These compounds have the formula:

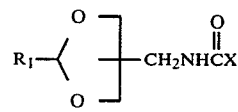

in which
X is halomethyl, wherein halo is selected from the group consisting of chlorine, bromine, and iodine and the methyl group is mono-, di-, or tri-substituted; and
$R_1$ is selected from the group consisting of lower alkyl having 1–4 carbon atoms, inclusive, and alkenyloxy having from 2–6 carbon atoms, inclusive, provided that, if $R_1$ is alkyl the haloacetylaminomethyl moiety is attached to the ring at the 2-position.

All carbon ranges are inclusive of both upper and lower limits. Exemplary of alkyl are methyl, ethyl, and the like. The term "alkenyloxy" includes moieties having at least one olefinic bond. Exemplary is allyloxy.

In preferred embodiments, X is chloromethyl and R is allyloxy; or X is dichloromethyl and R is methyl.

This invention also embodies a two-part herbicidal system comprised of
(a) an herbicidally effective amount of a thiocarbamate compound of the formula

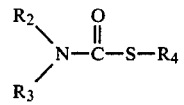

in which
$R_2$ is alkyl having 1–6 carbon atoms, inclusive;
$R_3$ is selected from the group consisting of alkyl having 1–6 carbon atoms, inclusive; and cyclohexyl; or
$R_2$ and $R_3$ form indistinguishable parts of a single alkylene ring having 4–10 carbon atoms, inclusive; and
$R_4$ is selected from the group consisting of alkyl having 1–6 carbon atoms, inclusive; haloalkyl wherein halo is selected from the group consisting of chlorine, bromine and iodine and alkyl has 1–6 carbon atoms, inclusive; alkenyl having 2–6 carbon atoms, inclusive; haloalkenyl wherein halo is selected from the group consisting of chlorine, bromine and iodine and alkenyl has 2–6 carbon atoms, inclusive; benzyl; and halo-substituted benzyl, wherein halo is selected from the group consisting of chlorine, bromine and iodine; and (b) a non-phytotoxic antidotally effective amount of a compound of the formula

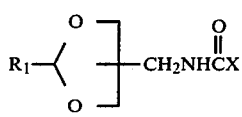

in which
X is halomethyl, wherein halo is selected from the group consisting of chlorine, bromine, and iodine and the methyl group is mono-, di-, or tri-substituted; and
$R_1$ is selected from the group consisting of lower alkyl having 1-4 carbon atoms, inclusive, and alkenyloxy having from 2-6 carbon atoms, inclusive, provided that, if $R_1$ is alkyl the haloacetylaminomethyl moiety is attached to the ring at the 2-position.

By way of exemplification, the active thiocarbamate herbicides employed in the invention may include the following: S-ethyl N,N-dipropyl thiocarbamate, S-ethyl N,N-diisobutyl thiocarbamate, S-propyl N,N-dipropyl thiocarbamate, S-propyl-N-butyl-N-ethylthiocarbamate, S-(2,3,3-trichloroallyl) N,N-diisopropyl thiocarbamate, S-ethyl N-ethyl N-cyclohexyl thiocarbamate, S-ethyl hexahydro-1H-azepine-1-carbothioate, isopropyl-1hexahydro-1,4-azepine-1-carbothioate, S-benzyl N,N-di-secbutylthiocarbamate, S-(4-chlorobenzyl) N,N-diethyl thiocarbamate and combinations thereof.

This invention also embodies a two-part herbicidal system comprised of
(a) an herbicidally effective amount of an acetanilide compound of the formula

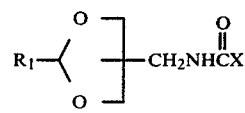

in which
$R_5$ and $R_7$ are independently selected from the group consisting of hydrogen; and alkyl having 1-6 carbon atoms, inclusive; and
$R_6$ is selected from the group consisting of alkyl having 1-6 carbon atoms, inclusive; alkoxy having 1-8 carbon atoms, inclusive; and carbethoxyalkyl wherein the alkyl group has 1-4 carbon atoms, inclusive; and
(b) a non-phytotoxic antidotally effective amount of a compound of the formula

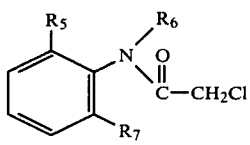

in which
X is halomethyl, wherein halo is selected from the group consisting of chlorine, bromine, and iodine and the methyl group is mono-, di-, or tri-substituted; and
$R_1$ is selected from the group consisting of lower alkyl having 1-4 carbon atoms, inclusive, and alkenyloxy having from 2-6 carbon atoms, inclusive, provided that, if $R_1$ is alkyl the haloacetylaminomethyl moiety is attached to the ring at the 2-position.

By way of exemplification, the active acetanilide herbicides employed in the invention may include: 2-chloro-2',6'-diethyl-N(methoxymethyl)acetanilide; 2-chloro-2'-methyl-6'-ethyl-N-(methoxypropyl-(2))acetanilide; 2-chloro-2',6'-dimethyl-N-(methoxyethyl)acetanilide; 2-chloro-2'-methyl-6'-ethyl-N-(ethoxymethyl)acetanilide; 2-chloro-N-isopropyl acetanilide; 2-chloro-2',6'-diethyl-N-(n-butoxymethyl)acetanilide; and 2-chloro-2-carbethoxymethyl-2',6'-diethyl acetanilide.

This invention also includes the method of establishing herbicidal selectivity which comprises applying to the locus where selectivity is desired an antidotally effective amount of a compound of the formula

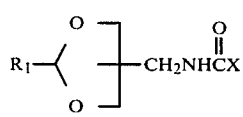

in which
X is halomethyl, wherein halo is selected from the group consisting of chlorine, bromine, and iodine and the methyl group is mono-, di-, or tri-substituted; and
$R_1$ is selected from the group consisting of lower alkyl having 1-4 carbon atoms, inclusive, and alkenyloxy having from 2-6 carbon atoms, inclusive, provided that, if $R_1$ is alkyl the haloacetylaminomethyl moiety is attached to the ring at the 2-position.

The locus where selectivity is desired may include soil, seeds, seedlings and vegetation.

Preparation

The thiocarbamates of the present composition are either commercially available or can be prepared by the procedures described in U.S. Pat. Nos. 2,913,327; 2,983,747; 3,133,947; 3,185,720; and 3,198,786.

The acetanilides of the present composition are either commercially available or can be prepared by the procedures described in U.S. Pat. Nos. 2,863,752; 3,442,945; 3,780,090; 3,937,730; 3,952,056; and 4,070,179.

The haloacetylaminomethyl dioxolane antidote compounds of this invention can be prepared according to the following general procedure, depending upon the starting materials. An appropriate chloroacetamide is reacted with an appropriate ortho ester or alcohol (preferably a diol) in a suitable solvent with an acid catalyst. Suitable solvents include dichloroethane. Suitable acid catalysts include ammonium chloride and β-naphthalene sulfonic acid. The reagents may be combined and refluxed. After cooling the reaction to room temperature, the reaction mixture may be stirred with a mild base, and then filtered. The filtrate may then be evaporated to yield the product. Structure may be confirmed by nuclear magnetic resonance (NMR) spectrometry.

EXAMPLE I (Compound No. 1)

Preparation of 2-allyloxy-4-(chloroacetylamino)methyl-1,3-dioxolane

Step 1: Preparation of N-(2,3-dihydroxypropyl)-chloroacetamide

One hundred-twenty grams (g) (1.0 mole) of methyl chloro acetate, 100 g (1.0 mole) of 3-amino-1,2-propanediol and 350 milliliters (ml) of ethanol were combined in a reaction flask and kept at about 0° C. for eight days. At the end of that time, the reaction mixture was removed from the refrigerator and evaporated. Yield was 173.2 g of N-(2,3-dihydroxypropyl)-chloroacetamide, a yellow oil. $n_D^{30} = 1.4900$.

Step 2: Preparation of 2-allyloxy-4-(chloroacetylamino)methyl-1,3 dioxolane

Six and seven-tenths g (0.04 mole) of N-(2,3-dihydroxypropyl)chloroacetamide, 7.3 g (0.04 mole) of triallylorthoformate, 0.2 g of ammonium chloride, and 50 ml of dichloroethane were combined in a reaction flask and distilled to a head temperature of 82° C. The distillate was cooled to room temperature, stirred with potassium carbonate and filtered over Florisil. The filtrate was evaporated to yield 3.2 g of 2-allyloxy-4-(chloroacetylamino)methyl-1,3-dioxolane, a yellow oil. Structure was confirmed by NMR. $n_D^{30} = 1.4888$.

EXAMPLE II (Compound No. 2)

Preparation of 2-methyl-2-(dichloroacetylamino)methyl-1,3-dioxolane

Step 1: Preparation of 3-(dichloroacetylamino)-2-propanone)

One g (0.0033 mole) of mercuric sulfate was combined with 2 ml of concentrated sulfuric acid and placed in a reaction flask. Twenty (20) ml of water and 120 ml of ethanol were added and the mixture was heated to 60° C. for 15 minutes.

Twenty g (0.12 mole) of N-(propargyl)-dichloroacetamide was added portion-wise at 60° C. with no apparent change in temperature. The reaction was heated for 1 hour and then allowed to stand at room temperature for several days.

The reaction mixture was filtered and evaporated to yield an oil which crystallized into a waxy solid. The waxy solid was extracted with methylene chloride and stripped to yield a brownish semi-solid. The semi-solid was triturated with ether-pentane.

Yield: 8.0 g of 3-(dichloroacetylamino)-2-propanone, an offwhite solid. m.p. = 89°–90° C. Structure was confirmed by NMR.

Step 2: Preparation of 2-methyl-2-chloroacetylamino)methyl-1,3-dioxolane

Six g of 3-(dichloroacetylamino)-2-propanone (0.03 mole), 2.0 g (0.03 mole) of ethylene glycol, 0.2 g of β-naphthalene sulfonic acid, and 100 ml of dichloroethane were combined in a reaction flask and refluxed until water stopped coming off. Then the reaction was stirred with potassium carbonate and filtered over Florisil. The filtrate was evaporated to yield 2.0 g of 2-methyl-2-(chloroacetylamino)methyl-1,3-dioxolane, a white solid. m.p. = 128°–130° C. Structure was confirmed by NMR.

The compounds prepared according to these procedures appear in Table I.

TABLE I

HALOACETYLAMINOMETHYL DIOXOLANE

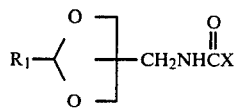

| Cmpd. No. | X | $R_1$ | Chemical Name | Physical Constant |
|---|---|---|---|---|
| 1 | ClCH$_2$ | O—CH$_2$—CH=CH$_2$ | 2-allyloxy-4-(chloroacetylamino)methyl-1,3-dioxolane | $n_D^{30}$ = 1.4888 |
| 2 | Cl$_2$CH | CH$_3$ | 2-methyl-2-(dichloroacetylamino)methyl-1,3-dioxolane | m.p. = 128–130° C. |

Testing

Stock solutions of the herbicides were prepared by diluting the requisite amount of each herbicide in water. Examples of solution compositions and application rates are summarized in Table II.

TABLE II

| | Herbicide Stock Solutions | | | |
|---|---|---|---|---|
| | Composition | | Application | |
| Herbicide Name | Herbicide (mg)* | Water (ml) | ml/flat** | lb/acre |
| VERNAM ® 6E | 292 | 300 | 5 | 1.00 |
| S—propyl N,N—dipropyl thiocarbamate | 2340 | 400 | 5 | 6.00 |

*The weight is measured in terms of mg of formulated herbicide. The formulations used contained about 72% active herbicide compound.
**The flats measure 5.95 inches by 9.5 inches. Approximately four (4) mg/flat is equal to one (1) lb/acre.

The herbicide was incorporated into the soil prior to planting or applied to the soil after planting and prior to the emergence of the plant. In some cases of preplant incorporation, the herbicide was either incorporated into the soil alone in preparation for in-furrow application of the antidote; in others the herbicide solution was tank-mixed with the antidote solution prior to incorporation.

Stock solutions of each antidote compound were prepared at the desired concentrations by diluting the requisite amounts of each antidote in acetone. An example of a solution composition, rate and application method is summarized in Table III.

TABLE III

Antidote Stock Solutions
Antidote: Haloalkylamino dioxolanes

| Composition | | Application | | |
|---|---|---|---|---|
| Antidote (mg) | Acetone (ml) | ml/flat | lb/acre | Method |
| 95 | 15 | 1.50 | 5.00 | IF* |

*IF = In-furrow surface application of antidote.

The antidote solutions were applied to the soil either by in-furrow surface application or by pre-plant incorporation. In all cases of pre-plant incorporation, the antidote was tank-mixed with the herbicide prior to incorporation into the soil.

For in-furrow application, a one pint (473 cubic centimeter (cc)) sample of soil containing the previously incorporated herbicide was removed and retained from each planting flat. After leveling and furrowing the soil, seeds of the crop or weed species were planted ½ inch deep (1.27 centimeter). Each flat was divided in half by a wooden barrier. A stock solution of the antidote was atomized directly onto the exposed seeds and soil in the open furrow on one side of the barrier. The seeds in the entire flat were then covered with the previously removed soil. The antidotally untreated sections of flats were compared for observed differences which would indicate lateral movement of the antidote through the soil.

Control flats contained crops treated with herbicide only.

All flats were placed on greenhouse benches where temperature was maintained between 70° and 90° F. (21.1° to 32.2° C.). The flats were watered by sprinkling as needed to assure good plant growth.

All of the soil used in the tests described herein was loamy sand soil treated with 50 parts per million (ppm) each of a commercially available fungicide, N-[(trichloromethyl)-thio]-4-cyclohexene-1,2-dicarboximide, and 18-18-18 fertilizer, which contains 18% by weight equivalent each of nitrogen, phosphorus pentoxide, and potassium oxide.

Injury ratings were taken four weeks after application of the antidote. The effectiveness of the antidote was determined by visual comparison of crop injury which occurred in the test flats to that which occurred in the control flats.

The treated crops initially screened for diminution of herbicidal injury were milo, wheat, cotton, rice, barley, corn and soybeans. Compounds which showed substantial activity were tested further. The weed species tested included watergrass (*Echinochloa crusgalli*) and foxtail (*Setaria viridis*).

KEY TO TABLES IV AND V

Compound numbers in these tables correspond to the numbers and their chemical description in Table I.

Herbicides

VERNAM ®—S-propyl N,N-dipropyl thiocarbamate
EPTAM ®—S-ethyl N,N-dipropyl thiocarbamate
LASSO ®—2-chloro-2',6'-diethyl-N-(methoxymethyl)acetanilide
TERIDOX ®—2-chloro-2',6'-dimethyl-N-(methoxyethyl)acetanilide

Application Methods

PES = Surface application of herbicide to soil after planting of seeds and prior to emergence of plants.
IF = In-furrow surface application of antidote (soil previously treated with herbicide only).
PPI = Pre-plant incorporation of herbicide or antidote. If both herbicide and antidote were preplant incorporated, a tank-mixed solution was used.
TM = Tank-mixed solution of herbicide and antidote.

If no antidote was applied, the word "none" appears in the Antidote Rate column. These are the control flats for each crop. The results shown on this line are the percent injuries sustained by each of the crops when treated with the herbicide only at the rate specified.

All rates shown, for both herbicide and antidote, are in pounds per acre.

Injury Ratings

The injury to the crop (Table IV) or weeds (Table V) is shown as a percentage of damage done to the plants as compared to an evaluation of the overall undamaged state of the plants. The damage done to the plants is a function of the number of plants injured and the extent of injury to each plant. This rating is made four (4) weeks after application of the herbicide alone or of the herbicide in combination with the antidote.

An asterisk (*) in Table IV indicates that the antidote compound is active in reducing herbicidal injury to the crop. Parentheses around a number indicate that the test has been run more than once and the results are inconclusive.

Table V shows that the antidote compound has no effect on weeds, i.e., herbicidal injury to the weeds is sustained even in the presence of the antidote compound.

TABLE III

Antidote Effectiveness

| Cmpd. No. | Herbicide | Herbicide Rate | Herbicide Method | Antidote Rate | Antidote Method | Milo % Inj | Wheat % Inj | Cotton % Inj | Rice % Inj | Barley % Inj | Corn % Inj | Soybean % Inj |
|---|---|---|---|---|---|---|---|---|---|---|---|---|
| 1 | VERNAM | 1.00 | PPI | none | — | 98 | 98 | 25 | 98 | 65 | | |
|   | VERNAM | 1.00 | PPI | 5.00 | IF | *70 | 98 | 25 | 98 | 65 | | |
|   | VERNAM | 6.00 | PPI | none | — | | | | | | 95 | 45 |
|   | VERNAM | 6.00 | PPI | 5.00 | IF | | | | | | *10 | 100 |
|   | VERNAM | 6.00 | PPI | none | — | | | | | | | 45 |
|   | VERNAM | 6.00 | PPI/TM | 1.00 | PPI/TM | | | | | | | 45 |
|   | VERNAM | 6.00 | PPI/TM | 2.00 | PPI/TM | | | | | | | 45 |
|   | VERNAM | 6.00 | PPI/TM | 5.00 | PPI/TM | | | | | | | 55 |
|   | EPTAM | 6.00 | PPI | none | — | | | | | | 75 | |
|   | EPTAM | 6.00 | PPI/TM | 0.05 | PPI/TM | | | | | | *(40) | |
|   | EPTAM | 6.00 | PPI/TM | 0.50 | PPI/TM | | | | | | *15 | |
|   | EPTAM | 6.00 | PPI/TM | 5.00 | PPI/TM | | | | | | *15 | |
|   | EPTAM | 6.00 | PPI | none | — | | | | | | 80 | |
|   | EPTAM | 6.00 | PPI/TM | 0.0125 | PPI/TM | | | | | | 80 | |
|   | EPTAM | 6.00 | PPI/TM | 0.025 | PPI/TM | | | | | | 80 | |
|   | EPTAM | 6.00 | PPI/TM | 0.05 | PPI/TM | | | | | | (80) | |

TABLE III-continued

| Cmpd. No. | Herbicide | Herbicide Rate | Herbicide Method | Antidote Rate | Antidote Method | Milo % Inj | Wheat % Inj | Cotton % Inj | Rice % Inj | Barley % Inj | Corn % Inj | Soybean % Inj |
|---|---|---|---|---|---|---|---|---|---|---|---|---|
| | LASSO | 3.50 | PES | none | — | 95 | 70 | | 100 | 70 | | |
| | LASSO | 3.50 | PES | 5.00 | IF | *60 | 70 | | *95 | 70 | | |
| | TERIDOX | 1.00 | PES | none | — | 100 | 70 | | | 80 | 100 | |
| | TERIDOX | 1.00 | PES | 5.00 | IF | 100 | 70 | | | 80 | *60 | |
| 2 | VERNAM | 1.00 | PPI | none | — | 95 | 95 | 40 | 90 | 80 | | |
| | VERNAM | 1.00 | PPI | 5.00 | IF | *75 | *60 | 40 | *60 | *55 | | |
| | VERNAM | 6.00 | PPI | none | — | | | | | | 90 | 30 |
| | VERNAM | 6.00 | PPI | 5.00 | IF | | | | | | *0 | 30 |
| | EPTAM | 6.00 | PPI | none | — | | | | | | 75 | |
| | EPTAM | 6.00 | PPI/TM | 0.05 | PPI/TM | | | | | | 75 | |
| | EPTAM | 6.00 | PPI/TM | 0.50 | PPI/TM | | | | | | *15 | |
| | EPTAM | 6.00 | PPI/TM | 5.00 | PPI/TM | | | | | | *0 | |
| | LASSO | 3.50 | PES | none | — | 95 | 70 | | 100 | 70 | | |
| | LASSO | 3.50 | PES | 5.00 | IF | *65 | *40 | | 100 | *50 | | |
| | TERIDOX | 1.00 | PES | none | — | 100 | 70 | | | 80 | 100 | |
| | TERIDOX | 1.00 | PES | 5.00 | IF | 100 | 70 | | | 80 | *80 | |

TABLE IV

| Cmpd. No. | Herbicide Name | Herbicide Rate | Herbicide Method | Antidote Rate | Antidote Method | Watergrass | Foxtail |
|---|---|---|---|---|---|---|---|
| 1 | VERNAM | 6.00 | PPI | none | — | 100 | 100 |
| | VERNAM | 6.00 | PPI/TM | 1.00 | PPI/TM | 100 | 100 |
| | VERNAM | 6.00 | PPI/TM | 2.00 | PPI/TM | 100 | 100 |
| | VERNAM | 6.00 | PPI/TM | 5.00 | PPI/TM | 100 | 100 |
| | EPTAM | 6.00 | PPI | none | — | 100 | 100 |
| | EPTAM | 6.00 | PPI/TM | 0.05 | PPI/TM | 100 | 100 |
| | EPTAM | 6.00 | PPI/TM | 0.50 | PPI/TM | 100 | 100 |
| | EPTAM | 6.00 | PPI/TM | 5.00 | PPI/TM | 100 | 100 |
| | EPTAM | 6.00 | PPI | none | — | 100 | 100 |
| | EPTAM | 6.00 | PPI/TM | 0.0125 | PPI/TM | 100 | 100 |
| | EPTAM | 6.00 | PPI/TM | 0.025 | PPI/TM | 100 | 100 |
| | EPTAM | 6.00 | PPI/TM | 0.05 | PPI/TM | 100 | 100 |
| | LASSO | 3.50 | PES | none | — | 100 | |
| | LASSO | 3.50 | PES | 5.00 | IF | 100 | |
| | TERIDOX | 1.00 | PES | none | — | 100 | |
| | TERIDOX | 1.00 | PES | 5.00 | IF | 100 | |
| 2 | EPTAM | 6.00 | PPI | none | — | 98 | 100 |
| | EPTAM | 6.00 | PPI/TM | 0.05 | PPI/TM | 98 | 100 |
| | EPTAM | 6.00 | PPI/TM | 0.50 | PPI/TM | 98 | 100 |
| | EPTAM | 6.00 | PPI/TM | 5.00 | PPI/TM | 98 | 100 |
| | LASSO | 3.50 | PES | none | — | 100 | |
| | LASSO | 3.50 | PES | 5.00 | IF | 100 | |
| | TERIDOX | 1.00 | PES | none | — | 100 | |
| | TERIDOX | 1.00 | PES | 5.00 | IF | 100 | |

Test Results

The compounds of this invention show good antidotal activity for a variety of crops. The composition of thiocarbamate herbicide and antidote compound was particularly effective for the reduction of herbicidal injury to corn crops. Use of the antidote compounds did not result in a reduction of herbicidal injury to weeds.

Formulations

A formulation is the incorporation of a formulant in a form which is directly usable on crops and weeds. As defined herein, a "formulant" is the material which is to be formulated. The formulant may be either an antidote compound alone or an herbicide and antidote composition. The purpose of the formulation is to apply the formulant to the locus where it is desired to establish herbicidal selectivity by a convenient method. The "locus" may include soil, seeds, seedlings and vegetation.

The formulations are commonly dusts, wettable powders, granules, solutions or emulsifiable concentrates.

Dusts are free-flowing powder compositions containing the formulant impregnated on a particulate carrier. The particle size of the carriers is usually in the approximate range of 30 to 50 microns. Examples of suitable carriers are talc, bentonite, diatomaceous earth, and pyrophyllite. The composition generally contains up to 50% of formulant. Anti-caking and anti-static agents may also be added. Dusts may be applied by spraying from boom and hand sprayers on airplanes.

Wettable powders are finely divided compositions comprising a particulate carrier impregnated with the formulant and additionally containing one or more surface active agents. The surface active agent promotes rapid dispersion of the powder in an aqueous medium to form stable, sprayable suspensions. A wide variety of surface active agents can be used, for example, long chain fatty alcohols and alkali metal salts of the sulfated fatty alcohols; salts of sulfonic acid; esters of long chain fatty acids; and polyhydric alcohols, in which the alcohol groups are free, omegasubstituted polyethylene glycols of relatively long chain length. A list of surface active agents suitable for use in agriculture formulations can be found in Wade Van Valkenburg, *Pesticide For-* mulations Marcel Dekker, Inc., N.Y., 1973) at pages 79–84.

Granules comprise the formulant impregnated on a particulate inert carrier having a particle size of about 1 to 2 millimeters (mm) in diameter. The granules can be made by spraying a solution of the formulant in a volatile solvent onto the granular carrier. Examples of suitable carriers for the preparation of granules include clay, vermiculite, sawdust, and granular carbon.

Emulsifiable concentrates consist of an oil solution of the formulant plus an emulsifying agent. Prior to use the concentrate is diluted with water to form a suspended emulsion of oil droplets. The emulsifiers used are usually a mixture of anionic and nonionic surfactants. Other additives, such as suspending agents and thickeners, may be included in the emulsifiable concentrate.

When the formulant is an antidote and herbicide composition, the proportion of antidote compound to herbicide compound generally ranges from approximately 0.001 to 30 parts by weight of the antidote compound per weight of the herbicide compound.

Formulations generally contain several additives in addition to the formulant and carrier or agent. Among these are inert ingredients, diluent carriers, organic solvents, water, oil and water, water in oil emulsions, carriers of dusts and granules, and surface active wetting, dispersing and emulsifying agents. Fertilizers, e.g., ammonium nitrate, urea and superphosphate, may be included. Aids to rooting and growth, e.g., compost, manure, humus and sand, may also be included.

Alternatively, the antidote compounds and herbicide and antidote compositions of this invention can be applied to a crop by addition of the formulant to irrigation water supplied to the field to be treated. This method of application permits the penetration of the compositions into the soil as the water is absorbed.

As another alternative, the formulant can be applied to the soil in the form of a solution in a suitable solvent. Solvents frequently used in these formulations include kerosene, fuel oil, xylene, petroleum fractions with boiling ranges above xylene and aromatic petroleum fractions rich in methylated naphthalenes. Liquid solutions, like dusts, may be applied by spraying from boom and hand sprayers on airplanes.

What is claimed is:
1. A herbicidal composition comprising:
(a) an herbicidally effective amount of an acetanilide compound of the formula

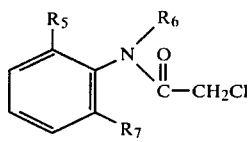

in which $R_5$ and $R_7$ are independently each alkyl having 1–2 carbon atoms, inclusive; and $R_6$ is alkoxyalkyl having 1–4 carbon atoms, inclusive; and (b) a non-phytotoxic antidotally effective amount of a compound of the formula

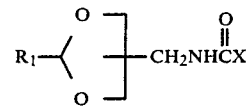

in which

X is halomethyl, wherein halo is selected from the group consisting of chlorine, bromine, and iodine and the methyl group is mono-, di-, or tri-substituted; and $R_1$ is selected from the group consisting of lower alkyl having 1–4 carbon atoms, inclusive, and alkenyloxy having from 2–6 carbon atoms, inclusive, provided that, if $R_1$ is alkyl the haloacetylaminomethyl moiety is attached to the ring at the 2-position.

2. A herbicidal composition as defined in claim 1 wherein X is chloromethyl, $R_1$ is allyloxy, and the haloacetylaminomethyl group is attached to the ring at the 4-position.

3. A herbicidal composition as defined in claim 1 wherein X is dichloro methyl, $R_1$ is methyl, and the haloacetylaminomethyl group is attached to the ring at the 2-position.

4. A herbicidal composition as defined in claim 1 wherein $R_5$ and $R_7$ are both ethyl and $R_6$ is methoxymethyl.

5. A herbicidal composition as defined in claim 1 wherein $R_5$ and $R_7$ are both methyl and $R_6$ is methoxyethyl.

6. A method of controlling undesirable vegetation and reducing herbicidal crop injury to corn, milo, rice, wheat and barley due to an acetanilide herbicide which comprises applying to the locus where control is desired a herbicidal composition comprising:
(a) an herbicidally effective amount of an acetanilide compound of the formula

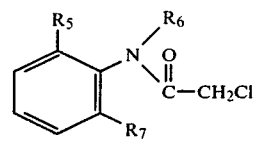

in which $R_5$ and $R_7$ are independently each alkyl having 1–2 carbon atoms, inclusive; and $R_6$ is alkoxyalkyl having 1–4 carbon atoms, inclusive; and (b) a non-phytotoxic antidotally effective amount of a compound of the formula

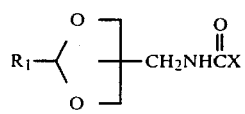

in which

X is halomethyl, wherein halo is selected from the group consisting of chlorine, bromine, and iodine and the methyl group is mono-, di-, or tri-substituted; and $R_1$ is selected from the group consisting of lower alkyl having 1–4 carbon atoms, inclusive, and alkenyloxy having from 2–6 carbon atoms, inclusive, provided that, if $R_1$ is alkyl the haloacetylaminomethyl moiety is attached to the ring at the 2-position.

7. A method as defined in claim 6 wherein X is chloromethyl, $R_1$ is allyloxy, and the haloacetylaminomethyl group is attached to the ring the 4-position.

8. A method as defined in claim 6 wherein X is dichloromethyl, $R_1$ is methyl, and the haloacetylaminomethyl group is attached to the ring at the 2-position.

9. A method as defined in claim 6 wherein $R_5$ and $R_7$ are both ethyl and $R_6$ is methoxymethyl.

10. A method as defined in claim 6 wherein $R_5$ and $R_7$ are both methyl and $R_6$ is methoxyethyl.

* * * * *